US011389600B2

(12) United States Patent
Besirli et al.

(10) Patent No.: US 11,389,600 B2
(45) Date of Patent: *Jul. 19, 2022

(54) APPLICATOR FOR CRYOANESTHESIA AND ANALGESIA

(71) Applicant: The Regents of The University of Michigan, Ann Arbor, MI (US)

(72) Inventors: Cagri Giray Besirli, Ann Arbor, MI (US); Stephen Smith, Mountain View, CA (US); Kevin P. Pipe, Ann Arbor, MI (US); Gun-Ho Kim, Ulsan (KR)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 194 days.

This patent is subject to a terminal disclaimer.

(21) Appl. No.: 16/273,252

(22) Filed: Feb. 12, 2019

(65) Prior Publication Data

US 2019/0167916 A1    Jun. 6, 2019

Related U.S. Application Data

(63) Continuation of application No. 16/136,416, filed on Sep. 20, 2018, now Pat. No. 10,238,814, which is a
(Continued)

(51) Int. Cl.
*A61M 5/42* (2006.01)
*A61F 7/00* (2006.01)
(Continued)

(52) U.S. Cl.
CPC .............. *A61M 5/422* (2013.01); *A61F 7/00* (2013.01); *A61F 7/007* (2013.01); *A61M 5/315* (2013.01);
(Continued)

(58) Field of Classification Search
CPC ................ A61F 7/00; A61F 2007/0001; A61F 2007/0004; A61F 2007/0075; A61F 2007/0087; A61M 5/422; A61M 5/427
See application file for complete search history.

(56) References Cited

U.S. PATENT DOCUMENTS 3,532,094 A    10/1970  Stahl
3,889,681 A     6/1975  Waller et al.
(Continued)

FOREIGN PATENT DOCUMENTS

CN    101068506 A    11/2007
CN    103099626 A     5/2013
(Continued)

OTHER PUBLICATIONS

Pain Physician, vol. 6, No. 3, pp. 345-360 (2003) "Cryoanalgesia in Interventional Pain Management" A.M. Trescot.
(Continued)

*Primary Examiner* — Laura A Bouchelle
(74) *Attorney, Agent, or Firm* — Harness, Dickey & Pierce, P.L.C.

(57) ABSTRACT

A handheld cryoanesthesia or analgesia device for cooling a target area on cutaneous membranes, mucous membranes, and tissue of the mucocutaneous zone having an elongated body and a thermoelectric cooling system disposed within the elongated body. The thermoelectric cooling system is configured to physically contact and thermally couple the target area of the cutaneous membranes, mucous membranes, and tissue of the mucocutaneous zone to induce cryoanesthesia or analgesia. The thermoelectric cooling system includes a thermally-conductive cold tip, a thermally-conductive cooling power concentrator thermally coupled to the cold tip, at least one Peltier unit module thermally coupled to the cooling power concentrator, a heatsink thermally coupled to at least one Peltier unit module, a power
(Continued)

source, at least one thermal sensor, and a controller operably outputting a control signal to the Peltier unit module to maintain a predetermined temperature.

3 Claims, 3 Drawing Sheets

Related U.S. Application Data continuation of application No. 15/079,132, filed on Mar. 24, 2016, now Pat. No. 10,322,248.

(60) Provisional application No. 62/237,793, filed on Oct. 6, 2015, provisional application No. 62/138,444, filed on Mar. 26, 2015.

(51) Int. Cl.
*A61M 5/315* (2006.01)
*A61M 5/32* (2006.01)
*A61M 5/20* (2006.01)
*A61F 9/00* (2006.01)

(52) U.S. Cl.
CPC .......... *A61M 5/322* (2013.01); *A61F 9/0008* (2013.01); *A61F 2007/0004* (2013.01); *A61F 2007/0052* (2013.01); *A61F 2007/0075* (2013.01); *A61F 2007/0078* (2013.01); *A61F 2007/0086* (2013.01); *A61F 2007/0087* (2013.01); *A61F 2007/0095* (2013.01); *A61M 5/20* (2013.01); *A61M 2005/206* (2013.01); *A61M 2202/048* (2013.01); *A61M 2210/0612* (2013.01)

(56) References Cited

U.S. PATENT DOCUMENTS

| | | | |
|---|---|---|---|
| 3,901,241 A | 8/1975 | Allen, Jr. | |
| 3,942,519 A | 3/1976 | Shock | |
| 4,440,167 A | 4/1984 | Takehisa | |
| 4,483,341 A | 11/1984 | Witteles | |
| 4,519,389 A | 5/1985 | Gudkin et al. | |
| 4,646,735 A * | 3/1987 | Seney | A61B 17/3211 128/DIG. 27 |
| 4,841,970 A | 6/1989 | Rand | |
| 5,314,423 A | 5/1994 | Seney | |
| 5,433,714 A | 7/1995 | Bloomberg | |
| 5,618,274 A | 4/1997 | Rosenthal | |
| 5,658,276 A | 8/1997 | Griswold | |
| 5,769,806 A | 6/1998 | Radow | |
| 5,916,212 A | 6/1999 | Baust et al. | |
| 5,921,963 A | 7/1999 | Erez et al. | |
| 6,017,337 A | 1/2000 | Pira | |
| 6,096,032 A | 8/2000 | Rowland | |
| 6,290,683 B1 | 9/2001 | Erez et al. | |
| 6,430,956 B1 | 8/2002 | Haas et al. | |
| 6,761,715 B2 | 7/2004 | Carroll | |
| 6,878,149 B2 | 4/2005 | Gatto | |
| 6,936,028 B2 | 8/2005 | Hommann et al. | |
| 7,037,326 B2 * | 5/2006 | Lee | A61F 7/007 606/20 |
| 7,229,468 B2 | 6/2007 | Wong, Jr. et al. | |
| 8,262,715 B2 | 9/2012 | Wong, Jr. et al. | |
| 8,480,664 B2 | 7/2013 | Watson et al. | |
| 8,523,930 B2 | 9/2013 | Saunders et al. | |
| 8,715,275 B2 | 5/2014 | Burger et al. | |
| 9,101,346 B2 | 8/2015 | Burger et al. | |
| 9,956,355 B2 | 5/2018 | Besirli et al. | |
| 10,238,814 B2 * | 3/2019 | Besirli | A61F 7/007 |
| 2005/0005626 A1 | 1/2005 | McMahon | |
| 2006/0200117 A1 | 9/2006 | Hermans | |
| 2007/0005016 A1 | 1/2007 | Williams | |
| 2007/0282282 A1 | 12/2007 | Wong et al. | |
| 2008/0045900 A1 | 2/2008 | Alchas et al. | |
| 2008/0051774 A1 | 2/2008 | Ofir et al. | |
| 2008/0086187 A1 | 4/2008 | Baxter et al. | |
| 2009/0264876 A1 | 10/2009 | Roy et al. | |
| 2010/0012566 A1 | 1/2010 | Nagaoka et al. | |
| 2010/0049126 A1 | 2/2010 | Bronfeld et al. | |
| 2010/0099771 A1 | 4/2010 | Asgharian et al. | |
| 2010/0174237 A1 | 7/2010 | Halaka | |
| 2011/0022115 A1 | 1/2011 | Salzhauer et al. | |
| 2011/0202048 A1 | 8/2011 | Nebrigic | |
| 2012/0128754 A1 | 5/2012 | Wei | |
| 2012/0310313 A1 | 12/2012 | Rogers et al. | |
| 2013/0066283 A1 | 3/2013 | Alster et al. | |
| 2013/0104569 A1 * | 5/2013 | Ballnik | A61F 7/007 62/3.2 |
| 2013/0116719 A1 | 5/2013 | Shtram et al. | |
| 2014/0228338 A1 | 8/2014 | Gadd et al. | |
| 2014/0303697 A1 * | 10/2014 | Anderson | A61B 18/02 607/104 |
| 2015/0051545 A1 | 2/2015 | Henderson et al. | |
| 2016/0242956 A1 | 8/2016 | Pilby Gomez | |

FOREIGN PATENT DOCUMENTS

| | | |
|---|---|---|
| DE | 2549922 A1 | 5/1977 |
| EP | 0043447 A2 | 1/1982 |
| FR | 2795629 A1 | 1/2001 |
| JP | 2004337296 A | 12/2004 |
| JP | 2005080832 A | 3/2005 |
| JP | 2013208314 A | 10/2013 |
| RU | 1835279 A1 | 8/1993 |
| WO | 2008081444 A2 | 7/2008 |
| WO | 2010/076355 A1 | 7/2010 |
| WO | 2010/129993 A1 | 11/2010 |
| WO | 2013139850 A1 | 9/2013 |
| WO | 2013/146780 A1 | 10/2013 |
| WO | 2014/102204 A1 | 7/2014 |
| WO | 2015008288 A1 | 1/2015 |

OTHER PUBLICATIONS

Med Tekh, vol. 6, pp. 24-27 (2007) "Development of a Cryogenic System and Tools for Surgery and Therapy" D. Miu.
Wiad Lek, vol. 56, No. 1-2, pp. 53-56 (2003) "The Application of Cryogenic Temperatures in Medicine" E. Birkner et al.
Anesthesia, vol. 36, No. 11, pp. 1003-1013 (1981) "Cryoanalgesia: The Application of Low Temperatures to Nerves to Produce Anesthesia or Analgesia" P.J. Evans.
Journal of Dermatologic Surgery and Oncology, vol. 6, No. 8, pp. 608-610 (1980) "Cryo Corner-Cryogenic Anesthesia and Hemostasis" L. Biro et al.
American Journal of Ophthalmology, vol. 112, No. 5, pp. 548-556 (1991) "Cold-Induced Corneal Edema in Patients with Trigeminal Nerve Dysfunction" K. H. Baratz et al.
International Search Report and Written Opinion dated Jul. 5, 2016 regarding PCT/US2016/023944.
Supplementary European Search Report dated Sep. 6, 2018 regarding 16769665.7.
ZimmerMedizinSysteme. "Zcryo—the new virtually painless concept (2014)" Published Nov. 19, 2014. Accessed Dec. 21, 2018. <https://www.youtube.com/watch?reload-9&time_continue=194&v=eWe77R3ty-U>.
Lucas B. Lindsell, et al. "Use of Topical Ice for Local Anesthesia for Intravitreal Injections." JAMA Ophthalmology, vol. 132, No. 8. Aug. 2014.
Department of Health & Human Services. "Correspondence of Mark N. Melkerson to Stefan Preiss." Feb. 24, 2006.
European Office Action regarding Application No. 16769665.7, dated Jan. 28, 2022.

* cited by examiner

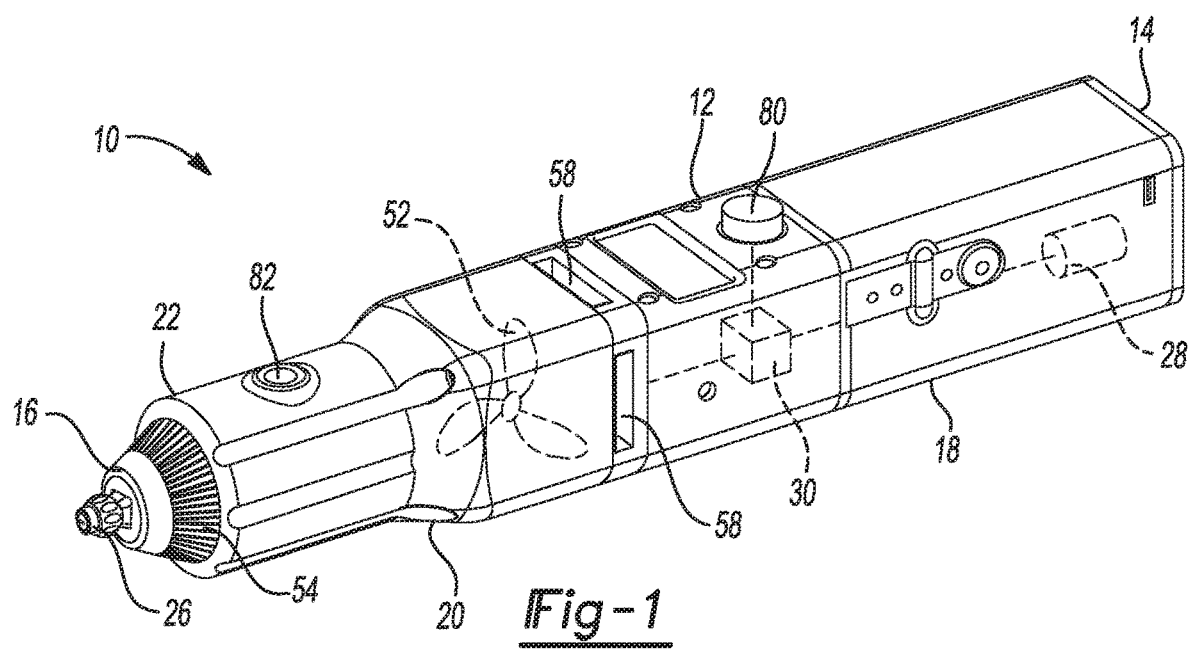
Fig-1
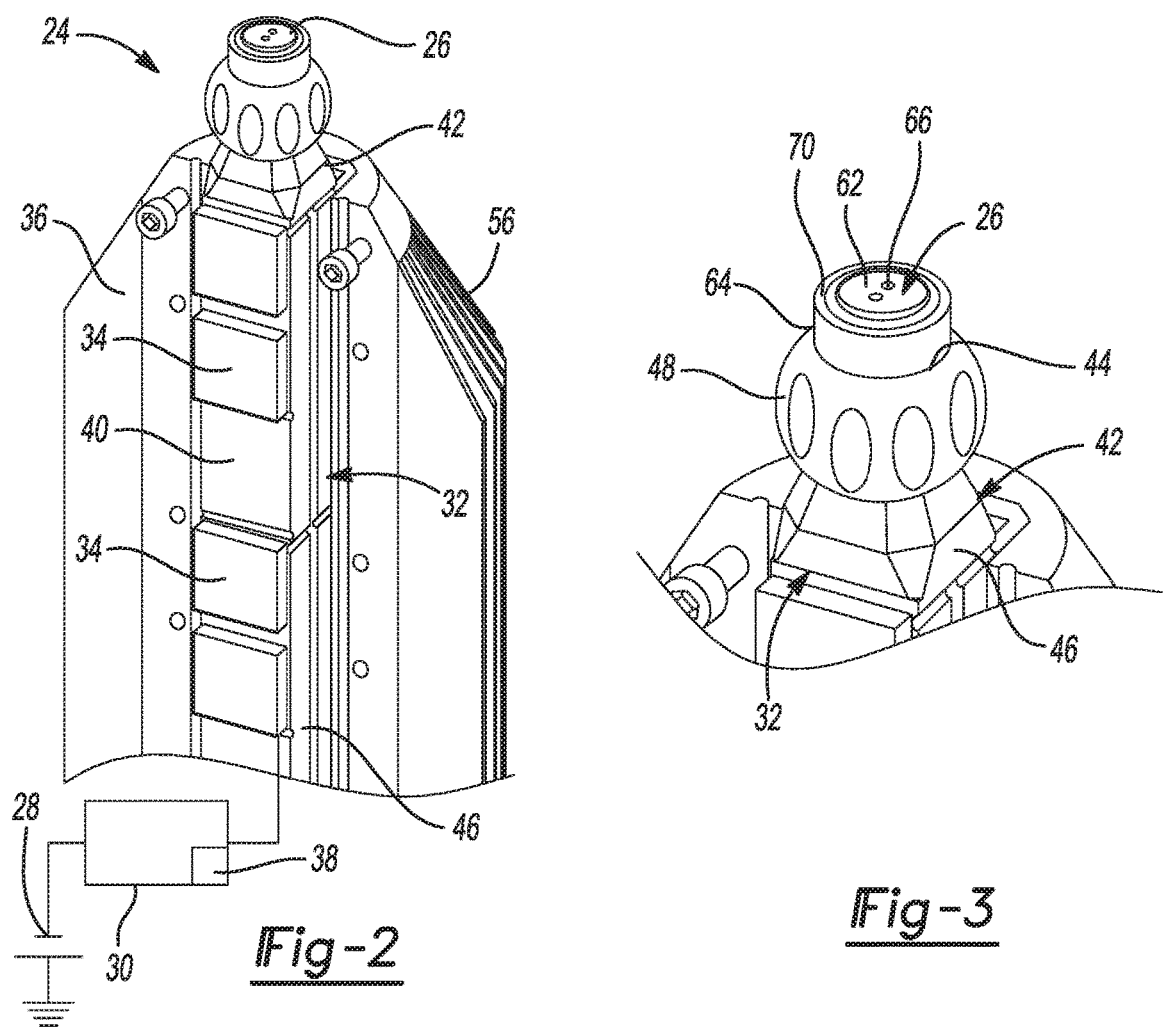
Fig-2
Fig-3

APPLICATOR FOR CRYOANESTHESIA AND ANALGESIA

CROSS-REFERENCE TO RELATED APPLICATIONS

This application is a continuation of U.S. application Ser. No. 16/136,416, filed on Sep. 20, 2018, which is a continuation of U.S. application Ser. No. 15/079,132, filed on Mar. 24, 2016, which claims the benefit of U.S. Provisional Application No. 62/237,793, filed on Oct. 6, 2015, and U.S. Provisional Application No. 62/138,444, filed on Mar. 26, 2015. The entire disclosures of the above applications are incorporated herein by reference.

FIELD

The present disclosure relates to a device to deliver rapid anesthesia or analgesia through cooling of biological tissue, such as cutaneous membranes, mucous membranes, or tissue of the mucocutaneous zone. In some exemplary embodiments, the cryoanesthesia device can deliver rapid anesthesia to the surface of the eye, or other biological tissue, at an injection site to enable more comfortable delivery of medication directly into the eye via intravitreal injection therapy (IVT), retrobulbar injection therapy, subtenon injection therapy, subconjunctival injection therapy, intracameral injection therapy, and the like.

BACKGROUND AND SUMMARY

This section provides background information related to the present disclosure which is not necessarily prior art. This section provides a general summary of the disclosure, and is not a comprehensive disclosure of its full scope or all of its features.

Pain is a major limiting factor in many common procedures performed in the inpatient and ambulatory care settings. A very abbreviated list includes skin biopsy, fine needle aspiration biopsy, IV insertion, vaccination, injections (including injection of anesthetics), blood draws, central line placements, and finger and heal pricks for blood analysis (glucose measurement). Pharmacologic anesthesia is a primary method of pain reduction, but the delivery of local pharmacologic anesthesia usually requires a painful injection. Other methods of providing anesthesia include the application of cold temperatures through ice, liquid evaporation, or low temperature substances. These methods of anesthesia are limited in part by the lack of temperature control and the inability to tightly focus the tissue area receiving anesthesia. The present device improves patient comfort by providing tightly controlled, focal cooling to the tissue needing anesthesia or analgesia.

The ocular surface is a tissue surface to which the present device can be applied, but is not limited to. The ability to deliver medication directly into the eye via intravitreal injection therapy (IVT) has transformed the treatment landscape of a number of previously blinding diseases, including macular degeneration and diabetic retinopathy. The success of these therapies in preventing blindness has resulted in a dramatic increase in the number of intravitreal injections performed, with an estimated 4.1 million injections given in the United States alone in 2013. The number of indications for IVT continues to expand, increasing utilization of this therapy significantly every year. The primary limitations of IVT are patient discomfort, ocular surface bleeding, and the time constraints of treating the vast number of patients requiring this therapy. These drawbacks relate to the difficulty of delivering ocular anesthesia to the highly vascularized ocular surface.

To give an ocular injection, the physician first provides ocular surface anesthesia by one of a number of methods, including the following: topical application of anesthetic drops; a subconjunctival injection of lidocaine; placement of cotton tipped applicators soaked in lidocaine above the planned injection site, placement of topical anesthetic gel, or some combination of these. Following ocular anesthesia, the physician or an assistant sterilizes the periocular region by coating it in betadine or a similar antiseptic. An eyelid speculum is then placed, and the physician marks the location of the injection using calipers that guide placement of the needle. The ocular surface is again sterilized, and the physician gives the injection.

Current methods of local anesthesia have unique drawbacks and patients often experience discomfort during and after intraocular injections. The number of indications for IVT continues to expand, increasing utilization of this therapy significantly every year. In light of this need, we have designed a device to deliver rapid anesthesia and vasoconstriction through the cooling of the surface of the tissue at the injection site, which will be discussed in greater detail herein.

Most patients receiving IVT receive multiple injections per year. In 2004, Friedman and colleagues applied age, ethnicity, and gender specific rates of AMD to the 2000 US census and estimated that 1.75 million Americans had exudate macular degeneration. Population based estimates suggest that this number will increase to 2.95 million or more by the year 2020. Using these same principles, Western Europe was estimated to have over 3.3 million patients with exudative macular degeneration in 2004. These numbers are likely underestimates of the true prevalence of disease. The majority of these patients are receiving IVT multiple times per year in one or both eyes. Recent studies have demonstrated that IVT is at least as successful as laser therapy to treat vision threatening retinal disease in patients with diabetic retinopathy and retinal vein occlusions, and this has resulted in wider adoption of IVT in these patients. The number of patients with treatable retinal diseases has increased steadily and will continue to grow over the next several decades. This has led to severe strain on clinic work flow, as IVT is a time-consuming procedure. Vitreoretinal surgeons perform these injections in busy clinics, frequently treating 60 to 70 patients per day. These injections are painful, and ophthalmologists typically choose one of two anesthesia options for IVT. The most common is to provide maximal anesthesia by one of two methods, which increases the time for patient preparation by several fold. The second option is to provide minimal anesthesia via topical drops, which is more time efficient, but results in significant patient pain. Both methods require a technician to prepare each patient. Developing a device to provide rapid anesthesia of the ocular surface will improve patient comfort and physician efficiency.

A recent case report and our own clinical experience show that excellent anesthesia is possible with the application of ice to the ocular surface. This therapy has been used for patients with allergies to lidocaine, but has much broader implications for all patients receiving IVT. Additionally, histopathologic safety data from historic studies of cryotherapy for the treatment of retinal tumors have shown that the operable temperature of the present device will not result in ocular tissue damage. Thus, the present device can improve patient comfort while simultaneously increasing physician efficiency delivering IVT.

Thermoelectric cooling provides reliable refrigeration as well as precise temperature control by direct electric feedback, which is hard to achieve with other available cooling techniques such as liquid evaporation, Joule-Thomson cooling, a thermodynamic cycle (e.g., a Stirling cooler or vapor compression refrigeration cycle), an endothermic reaction, or a low-temperature substance (e.g., liquid nitrogen). However, current thermoelectric (Peltier) modules have a low coefficient of performance (COP) and do not provide sufficient cooling power flux to maintain tissue at a temperature relevant for anesthesia (e.g., −5° C.) if a single unit is placed with its cooling surface in contact with tissue. As specified in the present teachings, the present device adopts a novel cooling power concentrator that collects the cooling power of multiple (or single) Peltier modules and concentrates this cooling over a small area, producing a sufficient cooling power flux required for rapid and sustainable low temperature cooling of tissue. In addition, the cooling power concentrator allows multiple Peltier modules to be distributed over a large area, minimizing the heat flux rejected from Peltier modules to the heat sink and hence relaxing the heat dissipation requirements of the heat sink.

According to the principles of the present teachings, a cryoanesthesia or analgesia device and method of use in ocular treatments is provided that allows for rapid administration of anesthesia to the eye, for example, for administration of intravitreal injections, for example. In some embodiments, by providing cooling of the conjunctiva and sclera at the injection site, patient discomfort is minimized.

In some embodiments, the cryoanesthesia device of the present teachings is designed to achieve a cold temperature quickly by means of a thermoelectric (Peltier) device, liquid evaporation, Joule-Thomson cooling, a thermodynamic cycle (e.g., a Stirling cooler or vapor compression refrigeration cycle), an endothermic reaction, and a low-temperature substance (e.g., liquid nitrogen). The cryoanesthesia device may be sufficiently sized to be handheld or be part of a larger unit, and may include safety mechanisms to limit cooling to a defined temperature, maximum heat flux, or time period in order to prevent damage to ocular or other biological tissue. In some embodiments, the cryoanesthesia device of the present teachings can comprise an applicator attached to a larger cooling unit. The cryoanesthesia device may be a stand-alone, hand-held unit. Use of the cryoanesthesia device of the present teachings improves anesthesia and reduces pre-injection prep time for patients and physicians.

It should be understood, however, that the cryoanesthesia device of the present teachings can be used to decrease pain in any part of the body, including, but not limited to, the cutaneous membranes, mucous membranes, and tissue of the mucocutaneous zone.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a perspective view illustrating a cryoanesthesia device in accordance with the principles of the present teachings;

FIG. 2 is a partial cross-sectional view illustrating the thermoelectric cooling system in accordance with some embodiments of the present teachings;

FIG. 3 is an enlarged perspective view of a cold tip of the cryoanesthesia device in accordance with some embodiments of the present teachings;

Corresponding reference numerals indicate corresponding parts throughout the several views of the drawings.

DETAILED DESCRIPTION

Figure 4:
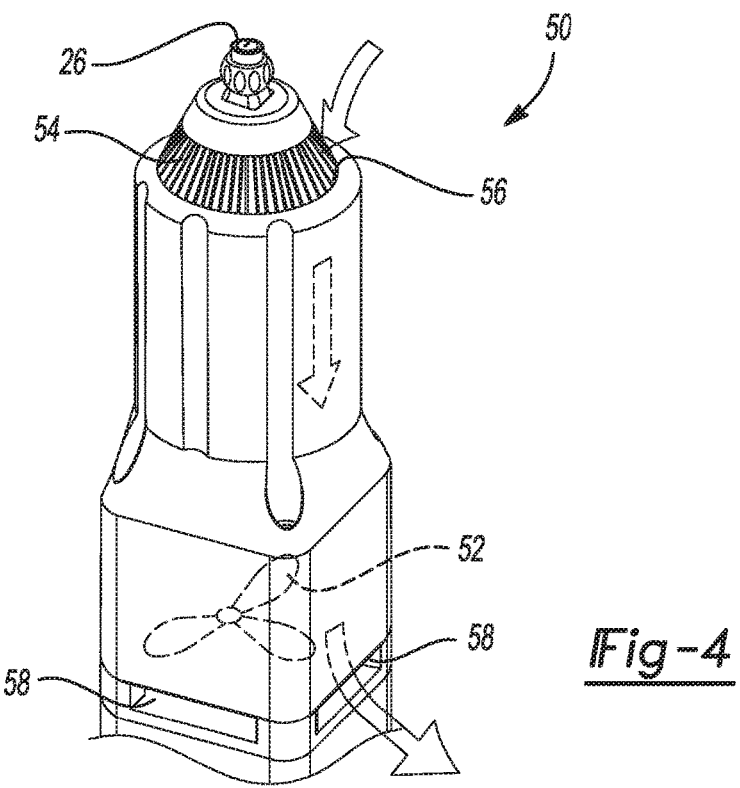
FIG. 4 is an enlarged perspective view of an air circulation system in accordance with some embodiments of the present teachings.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the cryoanesthesia device in use or operation in addition to the orientation depicted in the figures. For example, if the cryoanesthesia device in the figures is turned over, elements described as "below" or "beneath" other elements or features would then be oriented "above" the other elements or features. Thus, the example term "below" can encompass both an orientation of above and below. The cryoanesthesia device may be otherwise oriented (rotated 90 degrees or at other orientations) and the spatially relative descriptors used herein interpreted accordingly.

It should be understood that the present teachings will be described in connection with an eye. However, the principles of the present teachings are equally applicable for use with other biological tissue, including skin, organs, membranes, nasal mucosa, and the like. Accordingly, the disclosure should not be regarded as being limited to eyes, unless otherwise limited in the claims, but may include all biological tissue.

According to the principles of the present invention, a cryoanesthesia device is provided having advantageous construction and method of use. In some embodiments, the cryoanesthesia device is configured to provide rapid anesthesia to the ocular surface to aid in the administration of intravitreal injections or other medical procedures. Generally, the ocular surface is regarded as that portion of an eye that is exposed to the external environment. However, in some embodiments, the ocular surface can include the cornea and its major support tissue, the conjunctiva. In a wider anatomical, embryological, and also functional sense, the ocular mucosal adnexa (i.e. the lacrimal gland and the lacrimal drainage system) can be part of the ocular surface. The cryoanesthesia device of the present teachings rapidly achieves cold temperatures, such as through thermoelectric cooling, utilizing a thermodynamic cycle, utilizing an endothermic reaction, or the use of a cold substance such as liquid nitrogen to impart localized cooling to produce regional anesthesia. Such cryoanesthesia slows conduction of pain fibers in the conjunctiva (outermost layer of the eye) and the sclera (white of the eye).

The present teachings may have application in rapid, complete ocular anesthesia that can be given immediately prior to intravitreal injections, fine-needle aspiration biopsies, lacrimal and nasolacrimal system biopsies, and a wide variety of peri-ocular procedures including, but limited to, eyelid biopsies, peri-orbital injections of pharmacologic anesthetics, and eyelid lesion excisions. Accordingly, the present teachings provide numerous advantages, including but not limited to decreased time to achieve ocular anesthesia compared to current methods, more complete ocular anesthesia resulting in decreased pain from intravitreal injections, decreased ocular surface bleeding, and avoidance of the side effects of topical and injectable anesthetic medications.

The present teachings have application in rapid anesthesia of cutaneous membranes, mucous membranes, and tissue of the mucocutaneous zone. The cooling of nerve conduction can facilitate decreased pain prior to injections, IV placement, incisional and excisional biopsies, fine-needle aspiration biopsies, and a variety of other procedures including but not limited to finger sticks prior to glucose measurement.

With reference to the figures, a device 10 is provided having an advantageous construction and method of use for cryoanesthesia and/or analgesia (however, for brevity, device 10 will be referred to as cryoanesthesia device 10, but will have utility in both cryoanesthesia and analgesia applications). Specifically, in some embodiments as illustrated in FIGS. 1-4, cryoanesthesia device 10 can comprise an elongated body 12 having a proximal end 14 and a distal end 16. As will be appreciated from the foregoing description, cryoanesthesia device 10 can be sized and shaped to be a handheld portable device conducive to use in a wide variety of medical procedures in both in-patient and out-patient facilities. Elongated body 12 can be shaped to include a gripping portion 22 generally disposed at a balanced midpoint location and/or a location generally adjacent proximal end 14 or distal end 16. In the illustrated embodiment, gripping portion 22 is disposed generally between a midpoint location and distal end 16.

With continued reference to FIGS. 1-4, in some embodiments, elongated body 12 can comprise a neck portion 20 providing a transition between a proximal portion 18 and gripping portion 22. In some embodiments, gripping portion 22 can define a different cross-sectional shape relative to proximal portion 18 (e.g. a narrower shape), thereby resulting in neck portion 20 providing a transitional profile there between. It should be understood, however, that in some embodiments gripping portion 22 and/or proximal portion 18 can serve as a gripping portion to facilitate manipulation by a user. Therefore, the chosen nomenclature for proximal portion 18 and gripping portion 22 should not be regarded as limiting the invention, unless otherwise claimed. In some embodiments, cryoanesthesia device 10 is a handheld instrument measuring approximately 6 to 10 inches in length and 1 to 1.5 inches in diameter. However, alternative sizes are envisioned.

Generally, in some embodiments, cryoanesthesia device 10 cools a target area on the ocular surface to a predetermined temperature (e.g. in the range of about 5° C. to about −10° C.) within a predetermined amount of time (e.g. in the range of about 1 second to about 60 seconds, in the range of about 1 second to about 120 seconds, or longer), thereby inducing cryoanesthesia required for ocular procedures, such as intravitreal drug injection. It should be understood that other temperatures ranges are included in the present teachings, including predetermined temperatures in the range of about 5° C. to about −50° C. and in the range of about 5° C. to about −90° C. In some embodiments, cryoanesthesia device 10 comprises a thermoelectric (Peltier) cooling system 24 disposed within at least a portion of elongated body 12 for providing low temperature cooling of a cooling tip 26 disposed on distal end 16 of elongated body 12 to induce cryoanesthesia in the ocular surface. It should be understood that in some embodiments, a cooling system can comprise one or a combination of thermoelectric (Peltier) devices, liquid evaporation, Joule-Thomson cooling, a thermodynamic cycle (e.g., a Stirling cooler or vapor compression refrigeration cycle), an endothermic reaction, or a low-temperature substance (e.g., liquid nitrogen), which may or may not undergo a phase change.

In some embodiments, thermoelectric cooling system 24 comprises a cold tip 26, a power source 28, a controller 30, a cooling power concentrator 32, one or more Peltier unit modules 34, and a heat sink 36. It should be understood that, in some embodiments, thermoelectric cooling system 24 may include a heating element (not shown) that operates in conjunction with the cooling elements to precisely maintain a desired temperature and/or heat flux.

With particular reference to FIG. 3, in some embodiments, cold tip 26 can be made of a thermally conductive material, such as a metal, and can be sized to be generally equal to or smaller than the target area of the ocular or other biologic surface. In some embodiments, the target area on the eye is a region that begins at the corneal limbus and extends anywhere from 2 mm to over 8 mm posterior to the limbus. In some embodiments, the end of the cold tip 26 is circular, approximately 6 mm in diameter including thermally insulating outer ring member 64, which would correspond to the target area to be cooled. The thermally insulating outer ring member 64 restricts the area being cooled within the target area, which is touched by the thermally conductive cold tip 26, preventing damage to adjacent cells outside the target area. In some embodiments, the thermally insulating outer ring member 64 visually guides the target area but does not touch the ocular or other biologic surface to prevent heat exchange with the thermally insulating outer ring member 64. In some embodiments, a larger (or smaller) size of the cold tip can be used to provide anesthesia to cutaneous membranes, mucous membranes, or tissue of the mucocutaneous zone. In the illustrated embodiment, cold tip 26 is cylindrical in shape; however, it should be understood that alternative shapes are envisioned, including polygonal, oval, crescent, or any other conducive shape.

In some embodiments, power source 28 comprises a portable power source, such as a battery, capacitor, or similar device. In some embodiments, power source 28 can comprise a rechargeable lithium ion battery pack (28 Wh), which provides sufficient energy on a single charge to operate cryoanesthesia device 10 at −10° C. for approximately one hour. However, in some embodiments, power source 28 can comprise a non-portable power source.

Controller 30 can comprise a temperature regulating feedback loop to maintain highly accurate temperature control and/or a timed lockout mechanism to prevent excessive cooling. More particularly, in some embodiments, controller 30 can comprise a temperature sensor 38 operably coupled with at least one member of a thermal circuit comprising cold tip 26, cooling power concentrator 32, Peltier unit modules 34, heat sink 36, surrounding environment, and the ocular surface of the patient to output a temperature signal in response to a detected temperature. In this way, controller 30 receives the temperature signal and is operable to control an operating temperature of Peltier unit modules 34 via controlled current flow, controlled voltage, and/or pulse width modulation (PWM) of the DC battery source, thereby precisely regulating an operating temperature of cryoanesthesia device 10. In some embodiments, temperature sensor 38 is arranged to directly measure the temperature of the ocular surface of the eye or any portion of the thermal circuit using any one or a number of thermal sensors, such as but not limited to thermistors, thermocouples, and resistance or optical thermometers. Controller 30 can then compute temperature and/or heat flux. Controller 30 can maintain a predetermined temperature or temperature range using a constant value, a pulse of certain magnitude and duration, or a more complex prescribed pattern. In some embodiments, cryoanesthesia device 10 can automatically power off if the tip temperature falls below a certain temperature (e.g., −12° C.) to ensure a safe operating temperature range, and/or if a battery temperature exceeds 60° C. or the heat sink temperature exceeds 50° C. In some embodiments, controller 30 can operate on the basis of applied, measured, or desired heat fluxes rather than applied, measured, or desired temperatures.

As described, controller 30 may further comprise a timed lockout mechanism that monitors and controls, via an integrated timer, the duration of cooling. In this way, controller 30 is capable of monitoring and achieving sufficient cooling of the target area on the ocular surface and prohibit excessive cooling thereof. In some embodiments, this timed cooling lockout is set to a predetermined time of approximately 3 seconds to approximately 60 seconds; however, additional durations are anticipated by the present teachings. It should be understood that the timed lockout mechanism may be used in combination with the temperature regulating feedback loop to both actively monitor and control both a measured temperature and a measured time.

In some embodiments, cooling power concentrator 32 is a generally, but not limited to, elongated concentrator made of a thermally-conductive material, such as but not limited to metal. Cooling power concentrator 32 can be disposed along a central longitudinal axis of elongated body 12, and collects cooling powers of multiple Peltier units or that of a single Peltier unit. In some embodiments, cooling power concentrator 32 can be polyhedron in shape, and the cooling power collected from the surface(s) in contact with Peltier unit(s) is concentrated to one or more surfaces whose aggregate area is less than that of the Peltier unit cooling surface(s) at which collection occurs. However, it should be understood that cooling power concentrator 32 can have other shapes, including cylinder, cone, conical cylinder, sphere, hemisphere, or any other shapes that provide collecting and concentrating of cooling power. In such embodiments, Peltier unit modules 34 can be shaped to define a complementary surface to enhance surface area contact between Peltier unit modules 34 and cooling power concentrator 32 to facilitate thermoelectric cooling.

In some embodiments, cooling power concentrator 32 can be shaped to terminate at a compressible tip 42 that can be used to replace cold tip 26 prior to use and maintain its sterility. Compressible tip 42 can comprise a plurality of tapered flange members 44 extending radially from a main body portion 46 of cooling power concentrator 32. The plurality of tapered flange members 44 collectively form a central bore sized to receive cold tip 26 therein to provide a mechanical and thermal coupling there between. The plurality of tapered flange members 44 are sized and shaped to provide independent flexibility to provide the mechanical coupling of cold tip 26 in response to compression exerted via a compression ring 48 threadedly engaging corresponding threads disposed on an exterior surface of the plurality of tapered flange members 44. In this way, threaded engagement of compression ring 48 about the plurality of tapered flange members 44 results in the plurality of tapered flange members 44 being urged into a tighter, narrower nested relationship thereby exerting a compressive, retaining force upon cold tip 26. Accordingly, threaded manipulation of compression ring 48 about the plurality of tapered flange members 44 can provide selective coupling and decoupling of cold tip 26 with cooling power concentrator 32. It should be understood, however, that other fixture mechanisms such as a mechanical latch, magnetic coupling, bolt, or adhesive can be used to fix the cold tip. This is conductive to permitting cold tip 26 to be selectively replaced due to sterility and/or operational concerns. It should be understood that cold tip 26 is thus a replaceable tip that defines the contact cooling region of cryoanesthesia device 10 and provides a sterile surface for tissue contact. A replaceable or sterilizable tip coating 70 may also be integrated with cold tip 26 to provide a sterile surface for tissue contact.

In some embodiments, one or more Peltier unit modules 34 are disposed along, such as in an array, at least a portion of cooling power concentrator 32 to provide thermoelectric cooling of cooling power concentrator 32 and, thus, cold tip 26. It should be understood that Peltier unit module 34 can be configured as a single cooling element or a plurality of cooling elements. However, it should be understood that there are particular benefits to employing a plurality of Peltier unit modules 34, such as but not limited to redundancy of operation and the potential to source readily-available units from established industry. In some embodiments, the hot surface of Peltier unit module 34 is configured to be vertical with respect to central cooling portion 62 of cold tip 26. However, it should be understood that the hot surface of Peltier unit module 34 can be parallel or in any angle with respect to central cooling portion 62 of cold tip 26 depending on the desired direction of heat rejection from Peltier unit modules 34. In some embodiments, the plurality of Peltier unit modules 34 are operably coupled to power source 28 and controller 30 in such a way as to permit electrically parallel operation, thereby permitting cryoanesthesia device 10 to continue operation despite failure of one or more Peltier unit modules 34. In such a case, controller 30, and its associated feedback loop control system, can increase cooling output of the operable Peltier unit modules 34 to achieve desired cooling and/or duration performance.

While thermoelectric cooling has the advantages of being lightweight, small, solid-state (thus no fluids or moving parts), and electrically driven (thus allowing straightforward control of temperature), it rejects a large amount of heat that must be carefully managed. Cryoanesthesia device 10 provides a unique design for efficient heat spreading and dissipation. As described herein, cooling power concentrator 32 is thermally conductive and is cooled by one or more Peltier unit modules 34 to quickly and reliably maintain a predetermined temperature of cold tip 26. The Peltier unit modules 34 are distributed to efficiently spread the heat rejected from Peltier unit modules 34 to heat sink 36 and therefore promote efficient cooling, which reduces the size of heat sink 36 and may enhance visual clearance between cold tip 26 and a user's eye. Heat sink 36 is made of a thermally conductive material to efficiently spread the heat rejected from Peltier unit modules 34. In some embodiments, heat sink 36 is radially disposed about cooling power concentrator 32 and Peltier unit modules 34. In other words, heat sink 36 radiates outwardly from a central longitudinal axis of cryoanesthesia device 10. However, it should be understood that heat sink 36 can radiate heat in other directions depending on the relative angle of the hot surface of Peltier unit module 34 with respect to central cooling portion 62 of cold tip 26. In some embodiments, heat sink 36 is disposed generally within gripping portion 22 and/or neck portion 20 of elongated body 12, thereby providing localized heat sinking directly near Peltier unit modules 34 and cold tip 26, while maintaining a narrow shape of gripping portion 22 for improved visual clearance during use and handheld capability.

To facilitate heat dissipation from heat sink 36, an air circulation system 50 is provided for circulating air across fins or other features of heat sink 36. In some embodiments, a fan 52 (see FIG. 1) powered by power source 28 is actuated to draw air in from one or more inlet openings 54. In some embodiments, inlet openings 54 comprise a plurality of fin channels 56 formed in heat sink 36 that are used to increase the surface area of heat sink 36 to facilitate heat transfer. In some embodiments, the surface roughness of heat sink 36 can be large to further increase the surface area of heat sink 36 in contact with air. Air passes along the plurality of fin channels 46 formed in heat sink 36 and generally surrounded by gripping portion 22 of elongated body 12, along a direction generally, but not limited to, parallel to the central longitudinal axis of cryoanesthesia device 10, and exits from one or more outlet openings 58 at a location far from cold tip 26. It should be understood that the direction of air circulation can be perpendicular or in another angle to the central longitudinal axis of cryoanesthesia device 10 depending on the relative angle of the hot surface of Peltier unit modules 34 with respect to the surface of cold tip 26. Locating outlet openings 58 far from cold tip 26 not only reduces convection loss at the tip surface of cold tip 26, but also minimizes dryness of the patient's tissues due to airflow. Alternatively, air may be forced in the opposite direction and exit near the cold tip.

In some embodiments, cold tip 26 comprises a central cooling portion 62 being thermally coupled to cooling power concentrator 32, and a thermally-insulating ring member 64 surrounding a peripheral side of central cooling portion 62. Thermally-insulating ring member 64 is disposed to permit central cooling portion 62 to maintain an exposed contact tip configured to physically contact and thermally couple to a target area of the ocular surface, while simultaneously providing visual guidance regarding the position of the area to be cooled that is touched by the central cooling portion 62 with respect to the positions of nearby objects such as corneal stem cells and thereby prevent excessive cooling of these objects. In some embodiments, thermally-insulating ring member 64 includes an active heating element that controls the temperature adjacent to the cooled region in order to limit damage to surrounding tissue caused by cooling spread. In some embodiments, central cooling portion 62 of cold tip 26 defines an area of approximately 10 $mm^2$ to approximately 900 $mm^2$ (e.g. 3 mm×3 mm to 10×10 $mm^2$).

With continued reference to FIG. 3, in some embodiments, central cooling portion 62 of cold tip 26 can comprise targeting indicia 66 formed thereon configured to contact the target area of the ocular surface and provide a temporary marking for locating an anesthetized region. For example, in some embodiments, targeting indicia 66 can comprise a pair of protruding or indented features formed on cold tip 26 that temporarily results in markings on the ocular surface following removal of cryoanesthesia device 10. These markings can be then used to properly locate an anesthetized region for placement of the IVT needle (e.g., placement of the intravitreal injection needle 3 mm or 4 mm from the corneal limbus). It should be understood that different targeting indicia 66 are envisioned, including but not limited to a circular or ring-shaped protrusion, multiple protrusions, or any other shapes that provide temporary markings.

In some embodiments, cryoanesthesia device 10 can comprise a replaceable/disposable tip coating 70 to provide a sterile surface for ocular contact and to mitigate formation of an ice adhesion between cryoanesthesia device 10 and the patient's eye. In some embodiments, tip coating 70 can comprise a hydrophobic polymer layer to mitigate ice adhesion between the cryoanesthesia device and tissue.

In some embodiments, a first switch member 80 is provided for actuation of cryoanesthesia device 10. In some embodiments, switch member 90 can be used to set the cold tip temperature and timer duration, as well as power the Peltier modules. In some embodiments, operation of first switch member 80 comprises: 1) clockwise rotation to increase the cold tip set temperature, 2) counter-clockwise rotation to decrease the cold tip set temperature, 3) clockwise rotation while the first switch member 80 is pushed, to increase the timer duration, 4) counter-clockwise rotation while the first switch member 80 is pushed, to decrease the timer duration, and 5) double-pressing to activate the Peltier modules.

A second switch member 82 located near gripping portion 22 can be used to activate (or deactivate) the timer. When the timer is activated, cryoanesthesia device 10 can produce audible indicia, such as two consecutive beeping sounds at low and high frequencies followed by beeping sounds every 10 seconds during the timer duration, and finally two long consecutive beeping sounds at high and low frequencies when the timer duration has expired. In some embodiments, first switch member 80 can be pushed before the set time is reached to terminate the timer function. It should be understood that cryoanesthesia device 10 can comprise any one of a number of control inputs, indicia, and techniques; accordingly, the presently described inputs, indicia, and techniques should not be regarded as limiting the invention.

Figure 5A:
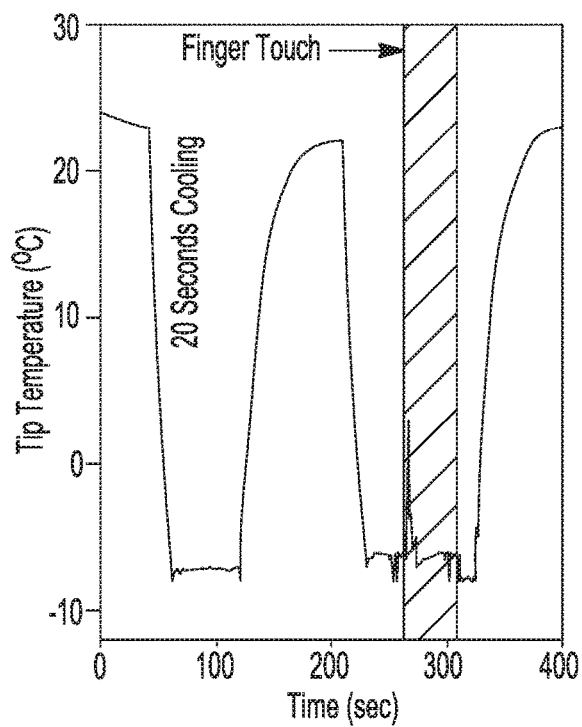
FIGS. 5A-5B are graphs illustrating simultaneously measured tip temperature, and power and voltage versus time.
Figure 5B:
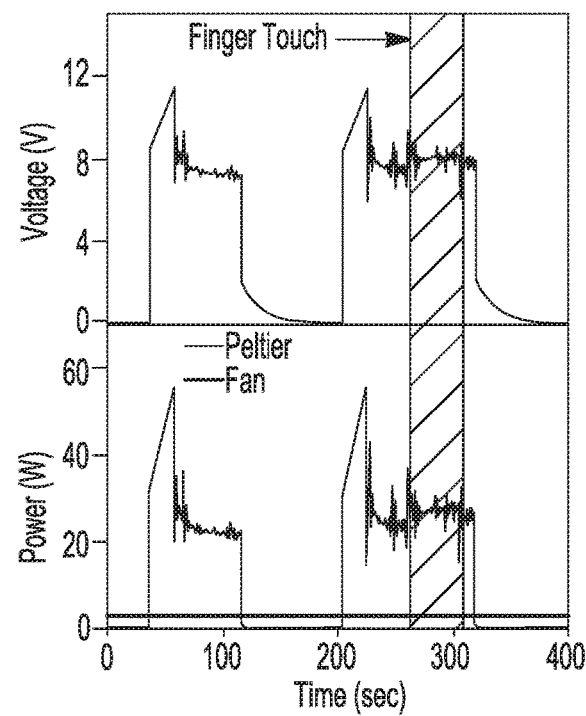

During use, in some embodiments, cryoanesthesia device 10 is positioned in contact with the patient's eye such that cold tip 26 (or tip coating) is in physical direct contact with the target area of the ocular surface. Cryoanesthesia device 10 can be actuated "ON" via switch 80 either before or after being placed in contact with the patient's eye. Actuation of cryoanesthesia device 10 thereby initiates rapid cooling of cold tip 26 by controller 30, cooling power concentrator 32, Peltier unit modules 34, heat sink 36, and air circulation system 50, while simultaneously marking the eye and anesthetizing the target area of the ocular surface. Following anesthetizing of the target area, a physician or care provider can then perform additional procedures, such as administering IVT. In some embodiments, a user may set a desired cold tip temperature and timer duration and then double-press first switch member 80 to activate Peltier modules 34 to bring cold tip 26 to a set temperature point (e.g. −10° C.). Cold tip 26 can then be brought into contact with the patient's eye and the timer actuated. Cryoanesthesia device 10 then maintains the set temperature point for a set predetermined duration (e.g. 10 seconds) and then produces indicia such as, but not limited to, beep sounds or vibration. After the timer duration, cryoanesthesia device 10 can automatically adjust the tip temperature to a higher temperature (e.g., −2° C.) to minimize ice adhesion between tissues and cold tip 26, and then return to ambient temperature. As illustrated in FIGS. 5A and 5B, tip temperature, along with power and voltage data, are illustrated along a time axis during operation.

Figure 6A:
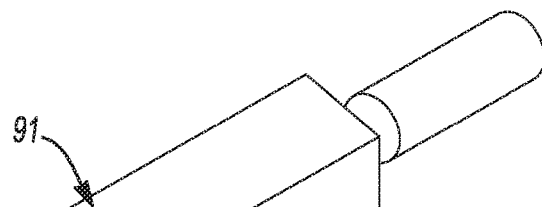
FIGS. 6A-6E is a series of perspective views of cryoanesthesia devices having an IVT needle, with portions removed for clarity, in accordance with some embodiments of the present teachings.
Figure 6B:
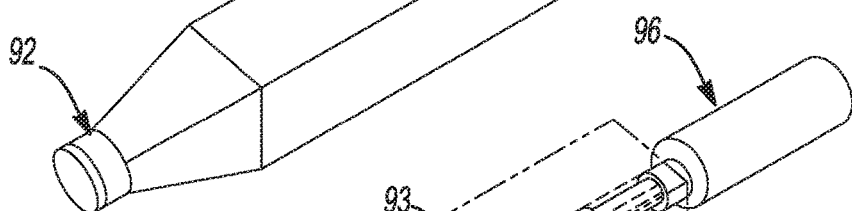
Figure 6C:
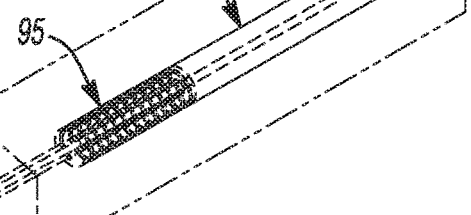
Figure 6D:
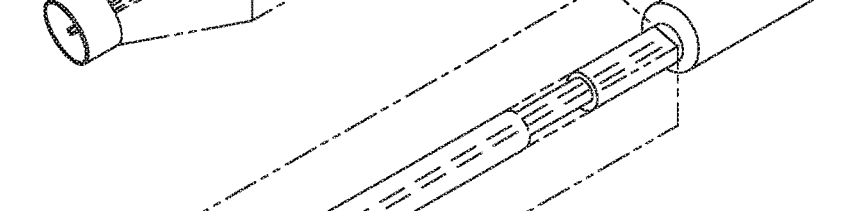
Figure 6E:
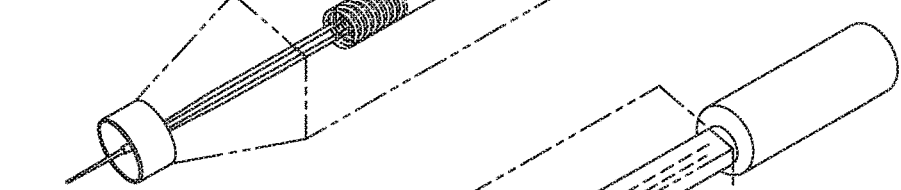
Figure 6E:
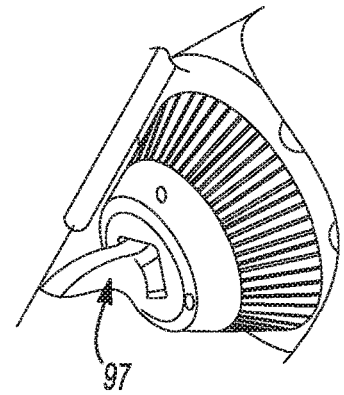

In some embodiments, as illustrated in FIGS. 6A-6E, the cryoanesthesia device performs both anesthesia and injection (e.g., intravitreal injection). In some embodiments, a cooling power concentrator 91 is sterilized and replaceable. In some embodiments, cooling power concentrator 91 first induces cryoanesthesia at a tip 92, after which the cryoanesthesia device performs injection (e.g., intravitreal injection). In some embodiments, a drug container 93 is placed inside the cooling power concentrator 91, as illustrated in FIG. 6B. In some embodiments, a solenoid 96 or similar feature pushes the drug container 93, compresses a spring 95 or similar feature, and inserts needle 94 within tissue (e.g., eye tissue). In some embodiments, solenoid 96 or similar feature controls the depth of needle insertion within tissue. In some embodiments, solenoid 96 or similar feature squeezes drug container 93, causing drug to be injected, as illustrated in FIG. 6D. In some embodiments, needle 94 is placed outside of cooling power concentrator 97, as illustrated in FIG. 6E. It should be understood, however, that the description above is provided for the purposes of illustration and does not limit the present teachings.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for cooling a target area of a cutaneous membrane, a mucous membrane, or tissue of a mucocutaneous zone, the device comprising:
   an elongated body having a gripping portion to facilitate handheld manipulation by a user, the elongated body having a proximal end and a distal end, the elongated body comprising:
   a cooling system configured to cool the target area to a temperature ranging between 0° C. and −80° C. to induce anesthesia or analgesia in the target area, wherein the cooling system comprises:
   a compression cooling system, and
   a temperature sensor and feedback loops to maintain tightly regulated temperature; and
   a controller for controlling the cooling system.

2. The device according to claim 1, wherein the target area is an ocular target area.

3. The device according to claim 1, wherein the target area is a cutaneous or mucocutaneous target area.

* * * * *